(12) United States Patent
Roesch et al.

(10) Patent No.: US 9,072,569 B2
(45) Date of Patent: Jul. 7, 2015

(54) MEDICAL AIR-DRIVEN HANDPIECE WITH ANTI-RETRACTION STOP

(75) Inventors: Thomas Roesch, Warthausen (DE);
Alexander Flock, Ulm (DE)

(73) Assignee: KALTENBACH & VOIGT GMBH, Biberach (DE)

( * ) Notice: Subject to any disclaimer, the term of this patent is extended or adjusted under 35 U.S.C. 154(b) by 335 days.

(21) Appl. No.: 13/423,530

(22) Filed: Mar. 19, 2012

(65) Prior Publication Data
US 2012/0244492 A1    Sep. 27, 2012

(30) Foreign Application Priority Data

Mar. 21, 2011   (DE) .......................... 10 2011 005 870

(51) Int. Cl.
*A61C 1/10* (2006.01)
*A61C 1/05* (2006.01)

(52) U.S. Cl.
CPC ...................................... *A61C 1/057* (2013.01)

(58) Field of Classification Search
USPC ........... 433/131, 132, 133, 125, 120, 114, 82, 433/85; 415/111, 112, 904
See application file for complete search history.

(56) References Cited

U.S. PATENT DOCUMENTS

| 3,310,285 A * | 3/1967 | Hawtin ............................. 415/1 |
| 2006/0127841 A1 * | 6/2006 | Teufelberger ................... 433/82 |

\* cited by examiner

*Primary Examiner* — Yogesh Patel
(74) *Attorney, Agent, or Firm* — Marshall, Gerstein & Borun LLP

(57) ABSTRACT

The invention relates to a medical turbine handpiece, in particular a dental turbine handpiece, having a drive shaft rotatably mounted in the front end region of the handpiece and to which a tool can be connected, as well as a turbine wheel arranged so as to be non-rotatable on the drive shaft and is arranged in a turbine chamber realized in the end region, into which turbine chamber a supply line for a flowing pressure medium for driving the turbine wheel opens out at an inlet opening and from which turbine chamber a removal line extends at an outlet opening, wherein at least one cross connecting channel for the pressure medium is realized in the wall of the turbine chamber, the cross connecting channel connecting the axially remote edge region of the turbine chamber to a region of the turbine chamber that is axially close to the drive shaft.

19 Claims, 6 Drawing Sheets

MEDICAL AIR-DRIVEN HANDPIECE WITH ANTI-RETRACTION STOP

RELATED APPLICATIONS

Priority is claimed to German Patent Application No. 10 2011 005 870.2, filed Mar. 21, 2011, the entire specification of which is hereby incorporated by reference herein.

BACKGROUND OF THE INVENTION

1. Field of the Invention

The invention relates to a medical handpiece for driving rotational medical tools, the tool being connectable to a drive shaft which is driven by a turbine arranged in the handpiece with the aid of a pressure medium. In a preferred manner, the pressure medium is compressed air.

2. Related Technology

In the case of such a turbine handpiece, a turbine wheel is mounted so as to be freely rotatable in a substantially round turbine chamber. The pressure medium is supplied by means of a supply line which extends longitudinally in the handpiece, flows through an inlet opening in the turbine chamber onto the turbine wheel, rotates the turbine wheel and leaves the turbine chamber by means of an outlet opening and a removal line which connects thereto. The drive of the turbine is shut down through the closing of a valve in the supply line. As the handpiece is operated at very high speeds, the turbine wheel still runs on for a considerable time after the supply of pressure medium has been cut out, forcing the pressure medium out of the turbine chamber into the removal line and consequently acting as a pump. The negative pressure generated at the same time in the turbine chamber causes a suction effect among other things in air gaps in the region of the mounting for the medical tools or in the region of the bearing arrangement of the turbine wheel. This is undesirable as pathogens can be sucked into the regions of the handpiece where only inadequate disinfection is possible or, in the worst case, which cannot be reached by way of the usual disinfection measures.

SUMMARY OF THE INVENTION

It has been shown, in particular, that a suction effect occurs preferentially in an axially close region of the turbine wheel, whilst in axially remote edge regions an overpressure is generated so that regions of the drive shaft or of the associated bearing region are contaminated with pathogens. Accordingly, the invention takes remedial action here and to minimize the ingress of outside air.

According to the invention, a medical turbine handpiece, in particular a dental turbine handpiece, is provided, having a drive shaft rotatably mounted in the front end region of the handpiece, to which a tool can be connected, as well as having a turbine wheel which is non-rotatably arranged on the drive shaft and is arranged in a turbine chamber realized in the end region, into which turbine chamber a supply line for a flowing pressure medium for driving the turbine wheel opens out at an inlet opening and from which turbine chamber a removal line extends at an outlet opening, wherein at least one cross connecting channel for the pressure medium is realized in the wall of the turbine chamber, this cross connecting channel connecting the axially remote edge region of the turbine chamber to a region of the turbine chamber that is axially close to the drive shaft.

The invention is consequently based on the idea of equalizing the pressure ratios in a region of the turbine chamber that is axially close to the drive shaft or to the axis of rotation of the turbine wheel or tool with the pressure ratios of an axially remote region and, at the same time, preventing the ingress of outside air into the turbine chamber. This can be realized in a preferred manner by way of a short connecting channel, i.e. essentially a connecting channel following a wall section of the turbine chamber, which enables a pressure medium exchange between the two said regions.

In a further development of the invention, the cross connecting channel extends through the wall of the turbine chamber separated from the turbine chamber.

This can be meaningful in particular in the case of wall sections of the turbine chamber which would result in elongation of the connecting path and thus would prevent a rapid air exchange.

In a preferred manner, the wall region of the turbine chamber is embodied in multiple parts. For example, the housing of the turbine handpiece can form a wall section of the turbine chamber and also a mounting element for the turbine wheel or the drive shaft, the mounting element, in a preferred manner, being realized so as to be connectable in a pressure-medium-tight manner to the housing. In this case, it can be provided that the cross connecting channel is arranged at least in sections in a wall section of the mounting element for the turbine wheel or the drive shaft, with corresponding bearing means.

In a further development of the invention, the mounting element is embodied in the form of a spray element for the discharging of a medical fluid.

Consequently, different advantages are produced in the production and assembly of the turbine handpiece, which clearly increase the possibilities for improving the air conduction and the pressure equalization. For example, it is possible to provide a spray element, which is realized at the same time as a mounting element for the drive shaft, with one or several cross connecting channels so that the mounting region of the drive shaft or of the turbine wheel can be moved rapidly to communicate with pressure medium from the axially remote edge region of the turbine chamber or of the turbine wheel. In particular it can be assumed that regions of the drive shaft with corresponding bearing means are difficult to disinfect and it is consequently particularly advantageous to prevent the ingress of outside air or serum into these regions.

In a particularly preferred manner, the cross connecting channel has an inlet opening and an outlet opening for the pressure medium, it being possible, for example, for the cross-section of the openings to be smaller than the length of the cross connecting channel. Consequently, it is possible to realize the pressure medium guiding means in the cross connecting channel as, in a preferred manner, a laminar flow which enables rapid pressure medium exchange between the two said regions.

A further aspect of the invention relates to a medical turbine handpiece, in particular a dental turbine handpiece, having a drive shaft that is rotatably mounted in the front end region of the handpiece, to which a tool can be connected, as well as having a turbine wheel which is arranged so as to be non-rotatable on the drive shaft and is arranged in a turbine chamber realized in the end region, into which turbine chamber a supply line for a flowing pressure medium for driving the turbine wheel opens out at an inlet opening and from which turbine chamber a removal line extends at an outlet opening, wherein the turbine wheel is confined in a manner sealed to pressure medium by means of a sealing face from a region close to the axis to an edge region remote from the axis of the turbine wheel, and a cross connecting channel is realized between the wall of the turbine chamber and the sealing face, this cross connecting channel connecting the edge region of the turbine chamber to a region of the turbine chamber which is axially close to the driving shaft.

In a preferred embodiment of the invention, the wall region of the cross connecting channel is realized in a substantially planar manner with faces that are parallel to each other so that a laminar flow behavior can also be promoted therewith. This can be realized, for example, by the sealing face of the turbine wheel, which, for example, follows a wall section of the turbine housing in a substantially parallel manner. For example, a cross connecting channel could also be realized in this way in the form of an annular channel.

In a further development of the invention, the wall region of the cross connecting channel has several projections or indentations of similar type.

In a preferred manner, the surface dimension of planar regions of the wall region exceeds the surface dimension of the projections or indentations.

Consequently, it is also possible to direct the flow and promote rapid pressure equalization. For example, by the projections or indentations, which, in a preferred manner, have a common direction of a preferred extension, it is possible to prevent or suppress the circulation of the pressure medium in a certain direction, for example transversely with respect to the preferred extension of the projections or indentations, so that a preferred direction of the circulation of the pressure medium is able to be achieved. For example, this can be particularly helpful for cross connecting channels whose inlet opening is larger than the outlet opening. In a particularly preferred manner, the projections or indentations are arranged in a wall region of the cross connecting channel, while an opposite wall of the cross connecting channel is planar in order, in this manner, to form the flow in an optimized manner with respect to the cross connecting channels.

In all the exemplary embodiments and aspects of the invention described, it is particularly useful that the equalization of a pressure difference of the pressure medium between the axially close region and the axially remote region of the turbine chamber is effected more rapidly than the ingress of outside air into the axially close region. Over and above this, it must be emphasized that the cross connecting channel is always an additional connection between the axially close and the axially remote regions of the turbine chamber, which is realized along with a connection between the inlet opening and the outlet opening, it also being possible to realize the latter, for example, by the air conduction in the turbine wheel itself.

BRIEF DESCRIPTION OF THE DRAWINGS

The invention is described in more detail below by way of the accompanying drawings, wherein identical elements are provided with identical reference numerals in all the representations, in which.

DETAILED DESCRIPTION

When medical devices are used, it is imperative that they can be held in a hygienically perfect state. In the case of medical handpieces, in particular dental handpieces for driving rotational medical tools, this is made particularly difficult.

Frequently, these handpieces have a complicated arrangement of communicating cavities which, for example, are formed by drive elements or by their receiving and supporting means. Over and above this; however, it is essential to create access to part of these receiving means or supporting means in order to ensure proper functionality of the handpiece as a result of maintenance measures. In particular, in the case of dental handpieces which have to ensure tool rotation of between 300,000 rpm and 450,000 rpm, a media-tight or serum-tight closure of all the cavities of the handpiece is consequently almost out of the question.

In particular in the dental sector, it is usual to use so-called turbine handpieces which accommodate a substantially freely rotatable turbine wheel in a turbine chamber to drive a rotational tool. The drive of the turbine wheel, in this case, is effected by a pressure medium. The pressure medium is supplied to the turbine chamber through an inlet opening by means of a supply line which extends longitudinally in the handpiece, flows onto the turbine wheel through an inlet opening in the turbine chamber, rotates the turbine wheel and leaves the turbine chamber by means of an outlet opening and a removal line which connects thereto. A positive additional effect of using a pressure medium having an elevated inherent pressure in relation to the surrounding pressure is that the ingress of outside air or serum in cavities and consequently also the contamination of the cavities by way of pathogens is effectively prevented.

It is possible to stop the drive of the turbines by interrupting the supply of pressure medium to the inlet opening of the turbine; on account of its mass inertia, the turbine wheel continues to rotate for a considerable period of time after the supply of the pressure medium has been interrupted, that is to say it runs on, so that the turbine develops a suction effect, among other things in gaps in the region of the mounting for the medical tools so that the risk of introducing external pathogens is greatly increased.

The invention is realized for the purpose of providing remedial action here.

Figure 1:
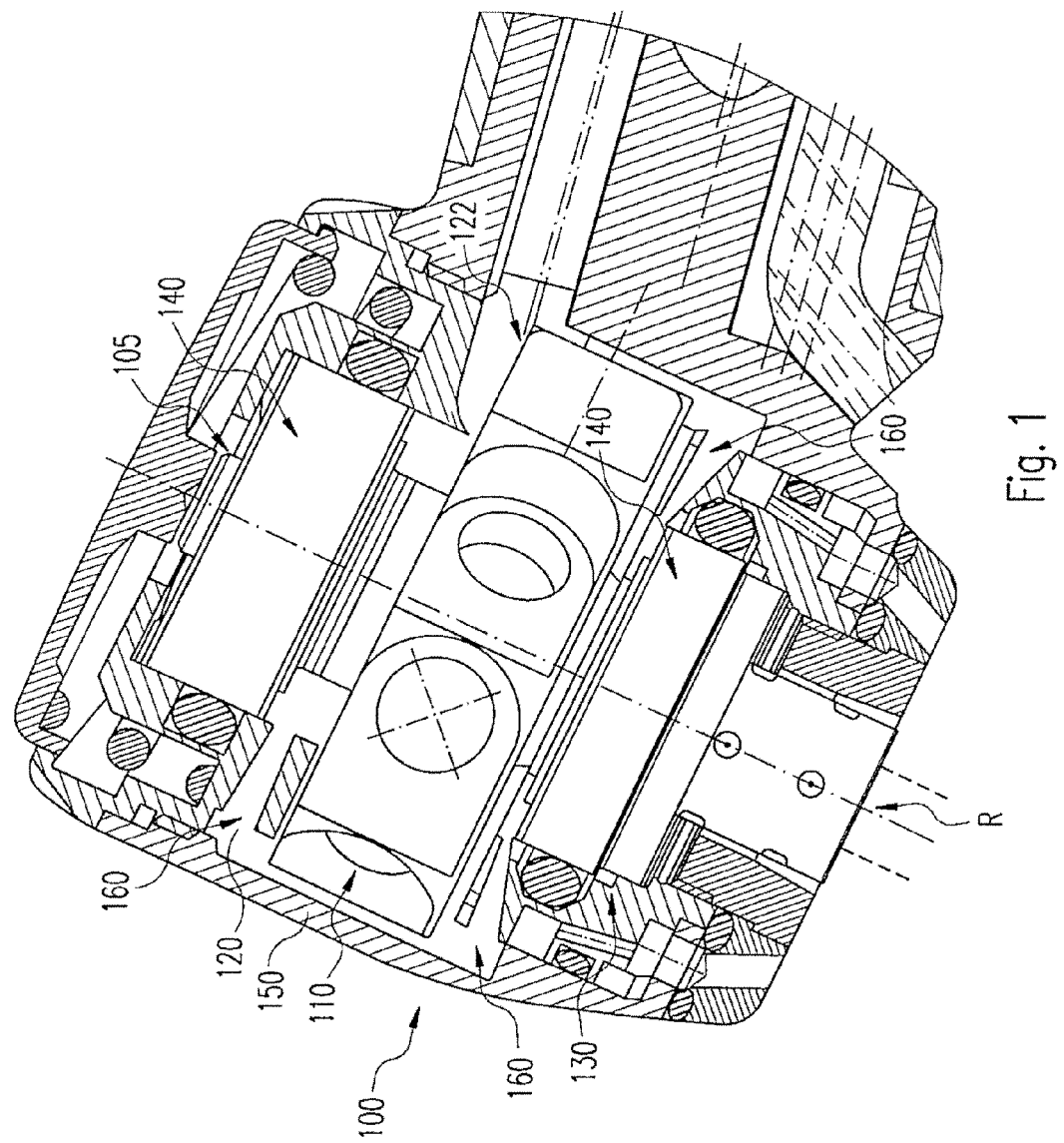
FIG. 1 shows an exemplary embodiment of a turbine handpiece in accordance with the invention.

FIG. 1 shows an exemplary embodiment of a dental turbine handpiece 100 in the form of a so-called angular handpiece. The handpiece has a housing 150, with an elongated handle region which is inclined with respect to the axis of rotation R of a dental tool. The invention is not limited to angular handpieces; other embodiments which, for example, can increase the accessibility of a treatment point with the medical tool are also conceivable. A drive shaft 105, which is mounted so as to be rotatable about the axis of rotation R of the tool and to which a medical tool, for example a drilling or polishing tool, can be connected, is arranged in the housing 150 in the front end region of the handpiece. The drive shaft 105 is mounted so as to be rotatable with respect to the housing 150 by means of high-performance roller bearings or ball bearings 140, the roller bearings or ball bearings 140, and thus also in an indirect manner the drive shaft 105, being connected to the housing by means of a holding element 130. A turbine wheel 110, which is arranged in a turbine chamber 120 realized in the end region, is connected in a non-rotatable manner to the drive shaft 105. An inlet opening 122 (not visible in FIG. 1) for a flowing pressure medium for driving the turbine wheel 110, and consequently the turbine, opens out into the turbine chamber 120, the pressure medium being fed to the turbine chamber 120 by means of a supply line which extends through the rear end region of the handpiece. Over and above this, the turbine chamber has an outlet opening 124, from which extends a removal line for the pressure medium that is also arranged in the rear end region of the handpiece.

In all the exemplary embodiments shown, compressed air is provided as the pressure medium; however, the invention is not limited to compressed air as the pressure medium. For example, other gases in particular nitrogen, or also liquid pressure media such as, for example, water could be provided; in a preferred manner this also depends on the application of the turbine handpiece, if, for example, special tools require cooling or the speed of the turbine is to be controlled, for example, by the viscosity of the pressure medium.

According to the invention, it is now provided that at least one cross connecting channel 160 for the pressure medium is realized in the wall of the turbine chamber 120, this cross connecting channel connecting an edge region of the turbine chamber 120 that is axially remote from the axis of rotation R to a region of the turbine chamber 120 that is axially close to the axis of rotation R or the drive shaft 105. The terms "axially close" or "axially remote," in this case, refer to the fact that an axially remote region is arranged further away radially from the axis of rotation R or the drive shaft 105 than an axially close region.

It has been shown, in particular, that an overpressure of the pressure medium is generated in the axially remote edge region of the turbine wheel 110 as a result of the geometry of the turbine wheel 110 during the "running-on" of the turbine, whilst a negative pressure is formed in an axially close region. The invention is now based on the idea of equalizing this pressure difference in a rapid manner before it can result in a foreign medium being sucked in, in particular, attempts being made in a preferred manner to connect the axially remote regions to the axially close regions in the shortest way. As will become clear below, over and above this other or additional measures that accelerate pressure equalization are also conceivable.

In the exemplary embodiment shown, outside air, for example, could be sucked in via gaps between the drive shaft 105 or roller bearings or ball bearings 140 and the housing 150 and could penetrate, for example, into the roller bearings 140 on which the drive shaft 105 is mounted so as to be rotatable about the axis of rotation R and which, without extensive measures, are only partly accessible for disinfection.

The wall region of the turbine chamber 120, in this case, substantially follows the circumferential form of the turbine wheel 110, the axis of rotation R of the tool or the drive shaft 105 coinciding with the longitudinal axis of the cylindrical circumferential form of the turbine wheel 110 or of the turbine chamber 120. The turbine chamber 120 now has cross connecting channels 160 which are essentially oriented in the radial direction and are guided, for example, in the form of slots in the wall of the turbine chamber.

Figure 2A:
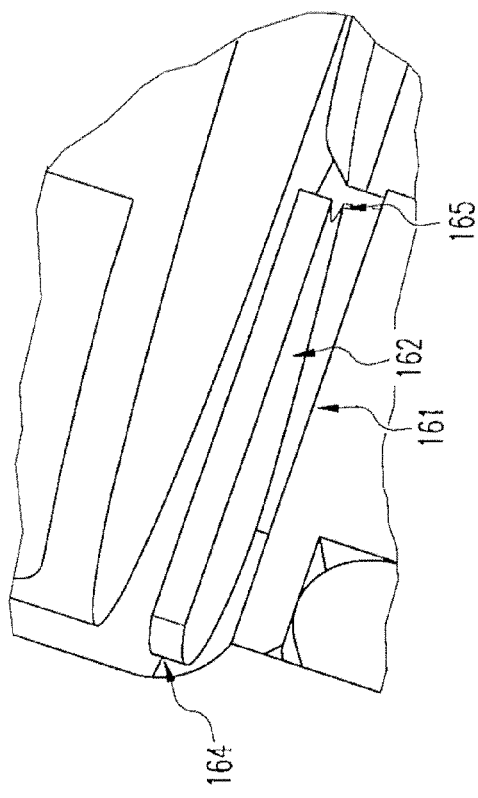
FIGS. 2 and 2a show details of the circulation of the pressure medium in the turbine handpiece.
Figure 2:
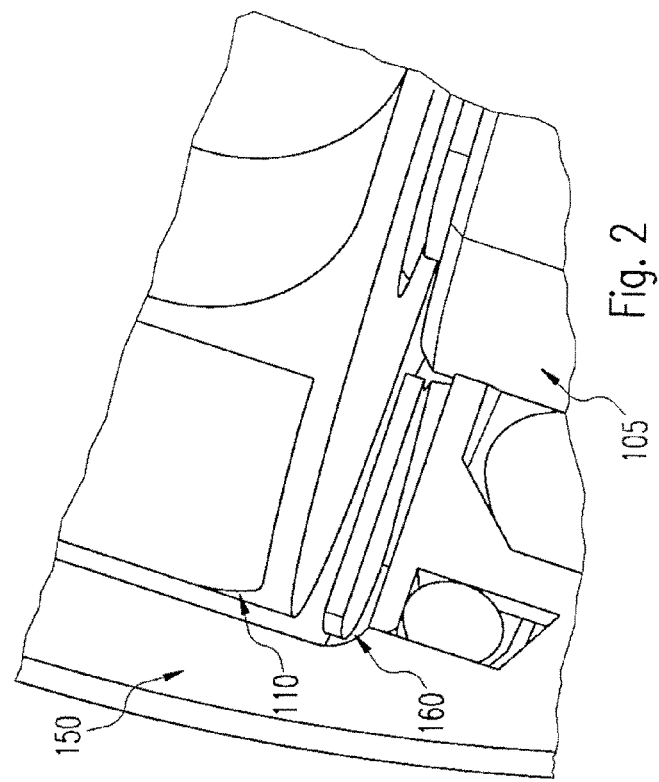

FIGS. 2 and 2a make this clear in a modification of the exemplary embodiment of FIG. 1. The cross connecting channel 160 or slot, in this case, has an inlet opening 164 and an outlet opening 165. The diameter of the inlet or outlet opening 164 or 165, in this case, is smaller than the length of the slot or the radial distance between the axially remote and axially close regions. By a relatively thin-walled separating web between the cross connecting channel 160 and the turbine chamber 120, which realizes a first wall region 162 of the cross channel 160, the pressure medium is separated, in this case, from the pressure medium guiding in the turbine chamber 120, in particular from a return channel 170 which supplies the pressure medium in the turbine chamber 120 to the outlet opening 124, so that independent flow conditions are able to form in the cross channel 160, this also being promoted by the above-described geometric conditions of the slot.

It is particularly advantageous in this case when a laminar pressure medium flow is set up for equalizing the pressure difference between the axially remote and the axially close regions, as, in this case, a particularly rapid pressure medium flow is possible. This can be promoted, in particular, by a second wall section 161 of the cross connecting channel 160 following the first wall section 161 in a substantially parallel manner. The first and second wall sections 162 or 161 are realized in a substantially planar manner; however, it can be helpful, as will subsequently become clear, to undertake a structuring of the wall sections 161 or 162 in order to set up preferred flow directions or to prevent unintended flows. The invention, as can also be seen from FIG. 1, is not restricted to the case described with the cross channel 160 having planar, preferably parallel wall faces. For example, the cross connecting channel 160 could also have a round or elliptical cross-section so that the preferred conditions which are favorable in terms of flow can be achieved for a rapid pressure medium flow.

As indicated in FIGS. 1, 2, and 2a, the wall of the turbine chamber 120 is realized in multiple parts. A first wall section of the turbine chamber 120, which essentially establishes the cylindrical circumferential surface of the turbine chamber 120, is formed, in this case, by the housing 150. The top surfaces of the turbine chamber 120, in this case, are sealed by mounting elements 130 for the roller bearings or ball bearings 140 of the drive shaft 105 or of the turbine wheel 110, which results in a series of advantages in the assembly and production of the turbine handpiece 100 so that, as a result, effective forms of the pressure medium guidance or of the formation of the cross connecting channel 160 are also able to be realized.

In particular, the cross connecting channel 160 can be guided at least in part in the mounting element or mounting elements 130 for the drive shaft 105 or for its bearings 140. This is shown again, for example, in an explicit manner in the exemplary embodiment of FIG. 3.

Figure 3:
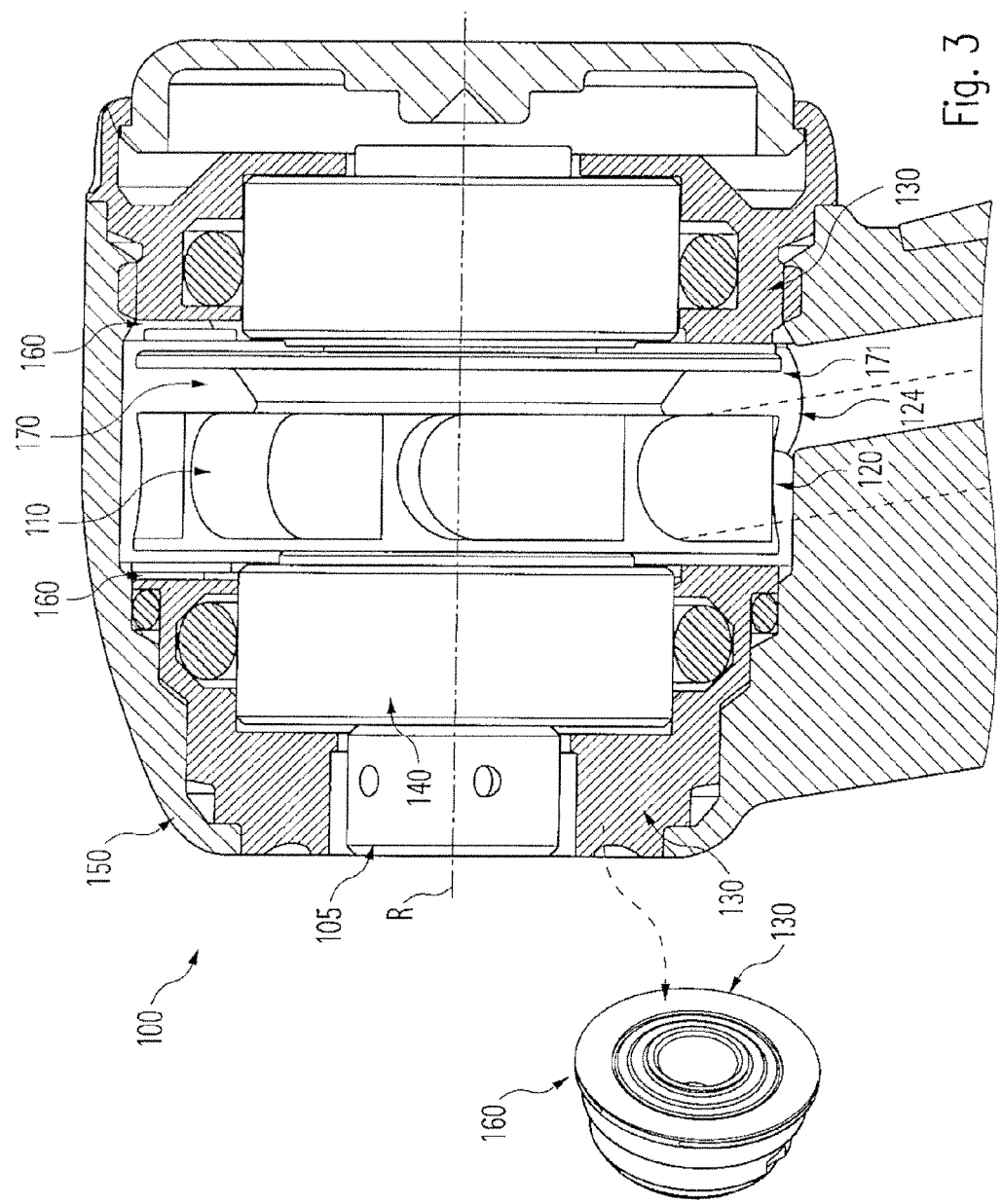
FIG. 3 shows a further exemplary embodiment of a turbine handpiece in accordance with the invention.

The turbine handpiece according to FIG. 3 has a first and second mounting element 130 which, in each case, seals the top sides of the cylindrical turbine chamber 120, and supports bearing means, in particular roller bearings or ball bearings 140, on which the turbine wheel 110 or the associated drive shaft 105 is mounted so as to be rotatable. The outside circumference of the mounting elements 130, in this case, can be approximated by a truncated cone shape, inlet openings 164 of several cross connecting channels 160 being provided in each case in the outside surfaces of the truncated cone or in the outer circumference, for example in a transverse or orthogonal manner with respect to the axis of rotation R, of the holding element 130.

Figure 4:
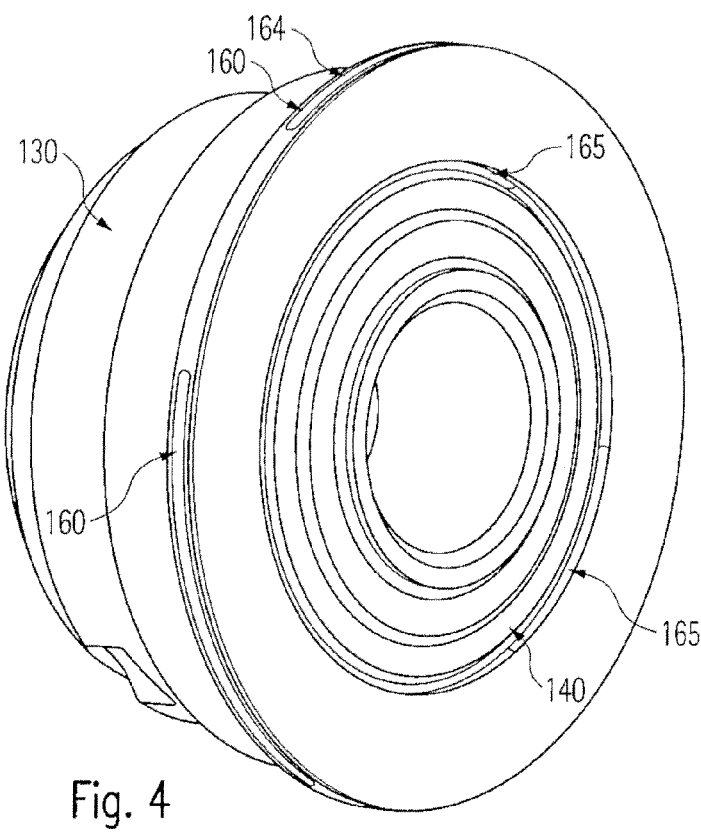
FIG. 4 shows details of a holding element for the turbine wheel.

The mounting elements 130 have one or more bores arranged concentrically or parallel to the axis of rotation R for the reception of the bearing means. Corresponding outlet openings 165 of the cross connecting channels 160, in this case, are connected to or open out into the said bores. This can also be found in particular in detail in FIG. 4.

The turbine wheel 110 shown in the exemplary embodiment in FIG. 3 realizes in the turbine chamber 120 an annular return channel 170 for the pressure medium by an annular flange 171, which is connected to the turbine wheel 110 and is arranged at a spacing from turbine blades of the turbine wheel 120, it consequently being possible to supply the pressure medium to the outlet opening 124 during the operation of the turbine by means of the return channel.

In particular, the cross connecting channel 160 is realized so as to be independent with respect to the return channel 170, which means that independence of the cross connecting channel 160 from flow conditions in the return channel 170 is able to be achieved.

The inlet opening 164 of the cross connecting channel 160, in this case, has a larger cross-sectional area than the corresponding cross-sectional area of the outlet opening 165 of the cross connecting channel 160. Consequently, with the cross-section of the cross connecting channel 160 continuously being adapted over its length, the pressure medium is accelerated over the course of the cross connecting channel 160. The approximately linear connection of the circumferential line of the inlet or outlet opening 164 or 165, in this case, establishes a cross-section of the cross connecting channel 160 which is almost trapezoidal radially with respect to the axis of rotation R which means that the cross-sectional area of the cross connecting channel 160 decreases over the length of its course.

In addition, several cross connecting channels 160 are realized in the exemplary embodiment distributed over the circumference of the turbine chamber 120. Consequently, several independent paths, in particular with independent flow conditions, can contribute to the connection between the axially close and axially remote regions, which achieve, for example, optimization of the pressure equalization even in the case of inhomogeneous pressure conditions in the edge region of the turbine chamber 120. As shown in particular in FIG. 4, over the circumference of its outside or outer surface the mounting element 130 has several, in this case three, inlet openings 164, which in each case are connected to cross connecting channels 160 which are guided separately in the mounting element 130. Corresponding outlet openings 165 of the cross connecting channels 160 open out in a common bore for the reception of bearing means for the drive shaft 105 or the turbine wheel 110.

Figure 5:
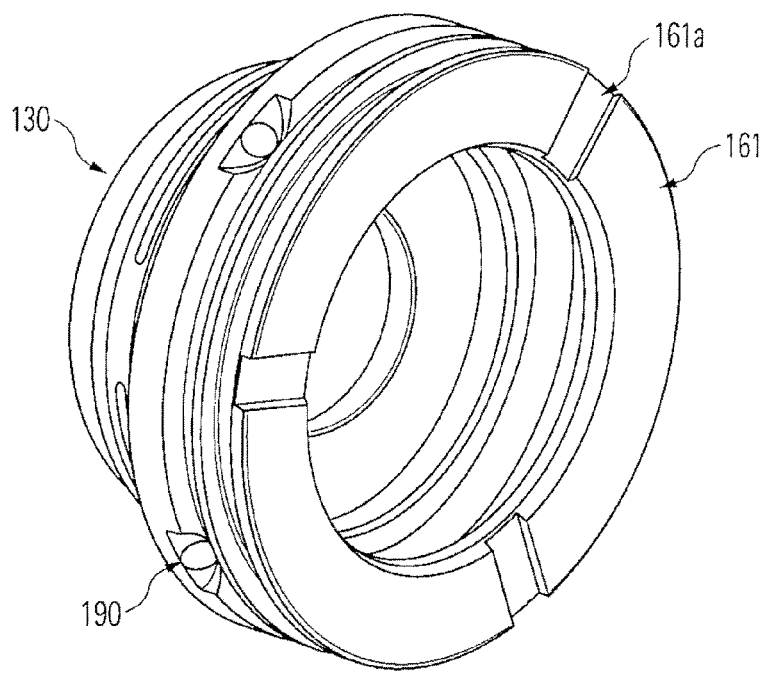
FIG. 5 shows details of a further exemplary embodiment of the holding element.
Figure 6:
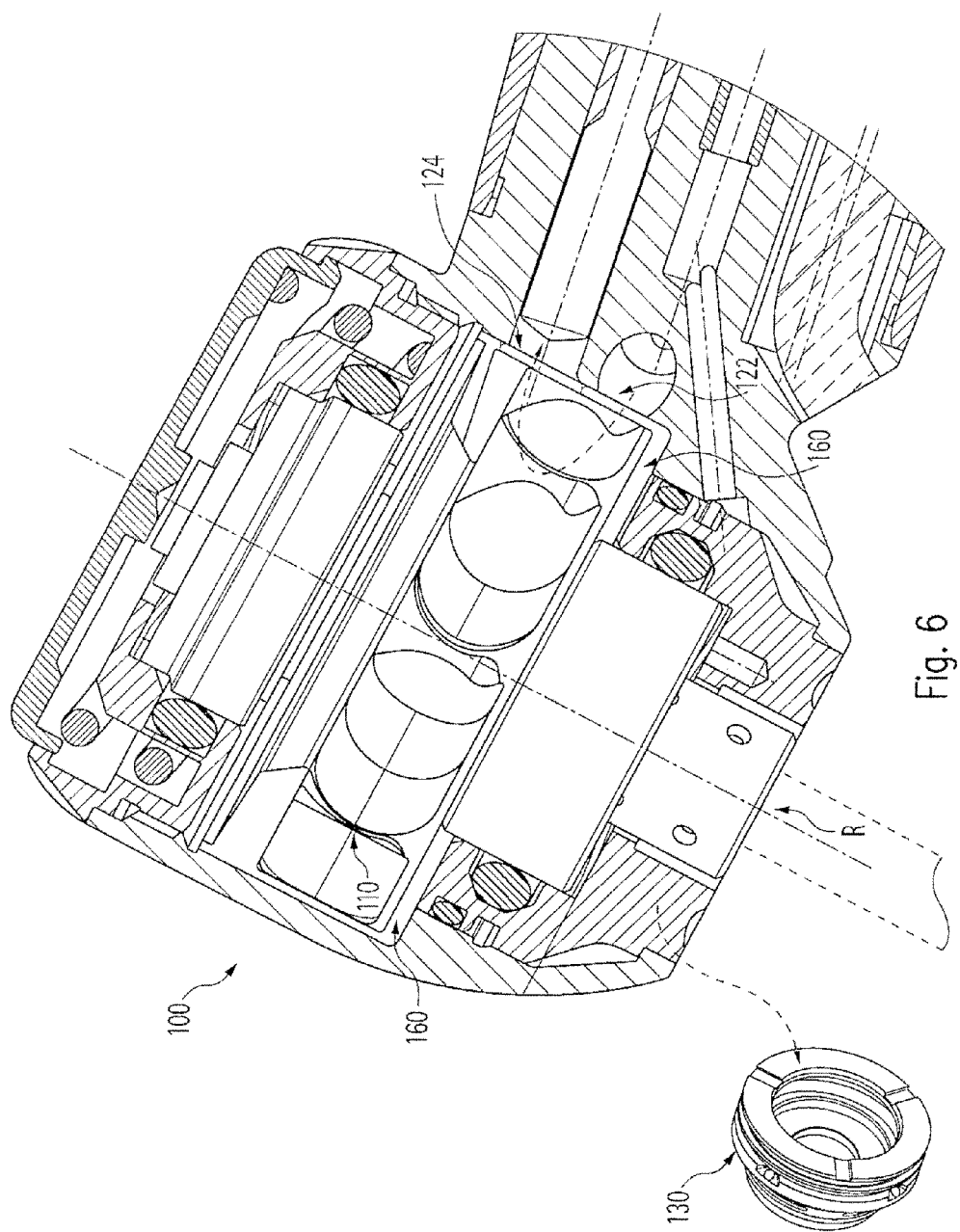
FIG. 6 shows the arrangement of the holding element according to FIG. 5 in an exemplary embodiment of the turbine handpiece.
Figure 7:
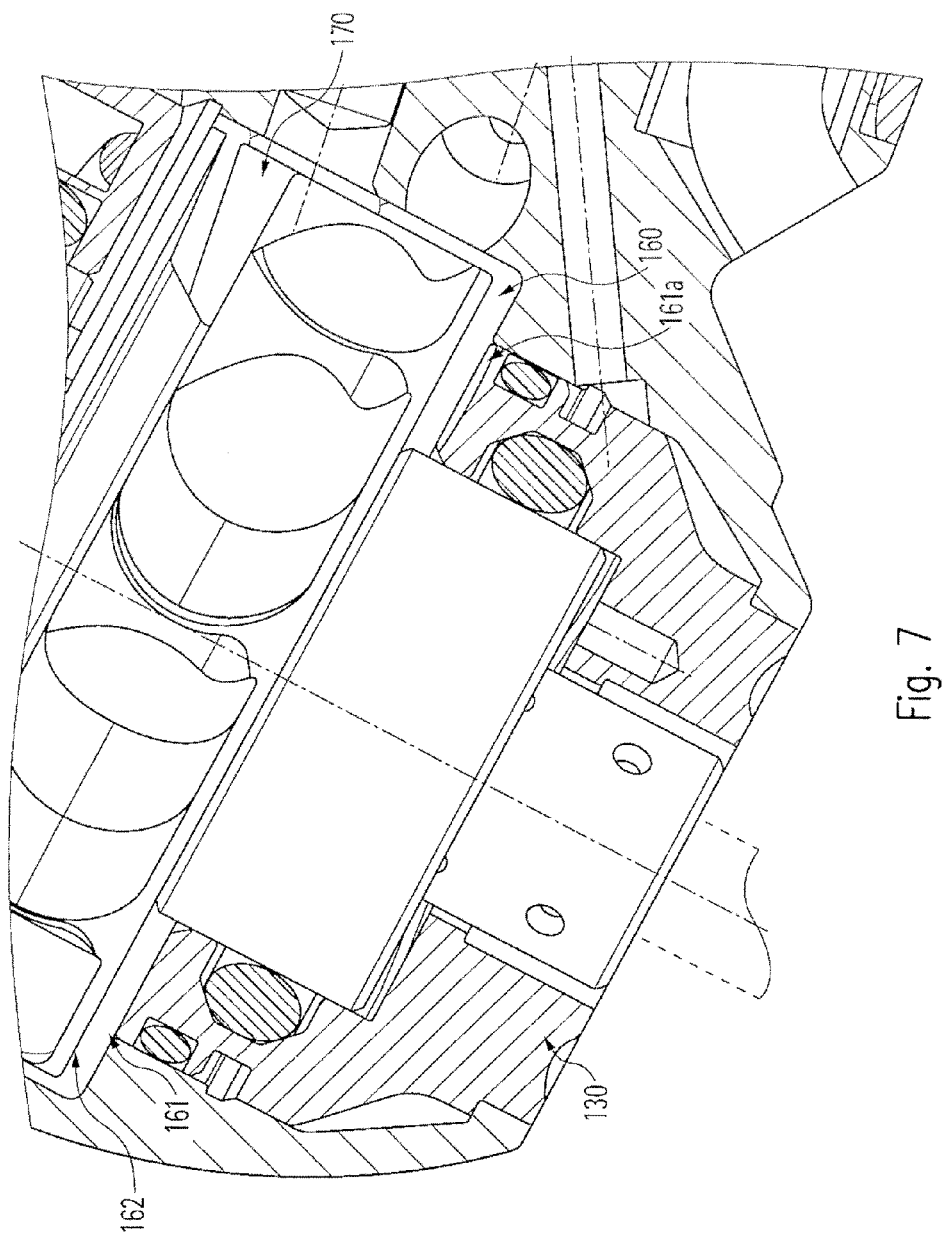
FIG. 7 shows details of the arrangement of the holding element shown in FIG. 6.

A further development of this concept and a further aspect of the invention is shown in the exemplary embodiment in FIGS. 5 to 7. FIG. 5, once again, provides a mounting element 130 which is realized at the same time as a spray insert for the outlet of a fluid from the turbine handpiece 100. Fluid channels 190, which are connected in operation to supply lines arranged in the handpiece 100, are provided in the mounting element 130 for this purpose. The mounting element 130, in this case, has independent seals for the connection of the fluid channels. Consequently, a fluid can be guided in the vicinity of the tool at the same time without there being any resultant risk of fluid being sucked into the turbine chamber 120 in the event of the turbine running on.

In addition, the mounting element 130 forms a substantially planar wall face 161 of the turbine chamber 120 which, in this case, is realized by a circular ring-shaped base of the mounting element 130.

A cross connecting channel 160 that is independent from a return channel 170 of the pressure medium can be realized, in this case, by a special design of the turbine wheel 110 so that the mounting element 130 or the wall of the turbine chamber 120 only forms one of the wall sections 161 of the cross connecting channel 160.

As is shown in particular in the exemplary embodiment in FIGS. 6 and 7, the turbine wheel 110 is defined by a sealing face so as to be sealed to pressure medium from an axially close region with reference to the drive shaft 105 as far as an axially remote edge region.

This sealing face forms a further wall section 162 of the cross connecting channel 160, so that a cross connecting channel 160 that connects the axially remote edge region of the turbine chamber 120 to an axially close region of the turbine chamber 120, is formed between the wall of the turbine chamber 120 and the sealing face. The exemplary embodiment shown consequently realizes a further annular channel which has planar wall sections and enables independent air conduction, separated from a return channel 170, and thus contributes to a rapid pressure exchange. In particular, the sealing face extends over its entire superficial extent substantially parallel to the opposite wall section of the turbine chamber 120 which completes the cross connecting channel 160.

A further development of the annular cross connecting channel 160 is also shown in FIGS. 5 to 7. Several elevations or indentation 161*a* of similar type can be provided in the planar, and in this example circular-ring-shaped, wall surface of the turbine chamber 120 over the circumference of the holding element 130 or of the wall of the turbine chamber 120, in a preferred manner distributed in an identical way. The elevations or indentations 161*a*, at the same time, can be used to realize a preferred direction of flow.

In the case of the annular cross connecting channel 160 of the described exemplary embodiment, for example a significant portion of pressure medium flowing in a rotating manner about the axis of rotation R is to be taken into consideration. However, a preferred laminar radial flow of the pressure medium is desirable for rapid pressure equalization. For this purpose, the wall of the turbine chamber 120 or the mounting element 130 has indentation slots which extend in a radial manner over the entire radial length of the, in this case, annular cross connecting channel 160 and lessen or prevent the formation of a portion of the flow of the pressure medium rotating about the axis of rotation R, for example by means of realizing local turbulence centers.

Along with the indentation slots described, it could be possible to provide radially arranged elevations at the same position, the radially arranged elevations being realized in an inverse manner to the indentation slots.

In each case, the plurality of elevations or indentations 161*a* which form a plurality of almost independent preferred directions of flow, establish a plurality of cross connecting channels 160 which are distributed over the circumference of the turbine chamber 120 and enable independent pressure equalization.

By way of the invention, therefore, an efficient possibility is created to realize pressure equalization between an edge region and a region of the turbine chamber 120 which is axially close to the axis of rotation R, so that the sucking in of foreign media through openings in the handpiece can be suppressed. In this case, it must be emphasized that the disclosed features of all the exemplary embodiments or aspects of the invention can be combined together.

The invention claimed is:

1. Medical turbine handpiece comprising:
    a drive shaft rotatably mounted in a front end region of the handpiece, to which drive shaft a tool can be connected, and
    a turbine wheel arranged non-rotatably on the drive shaft and arranged in a turbine chamber formed in the end region, into which turbine chamber a supply line for a flowing pressure medium for driving the turbine wheel opens out at an inlet opening and from which turbine chamber a removal line extends at an outlet opening, wherein at least one cross-connecting channel for the pressure medium is formed as a slot in a wall of the turbine chamber, the cross-connecting channel fluidly connecting an edge region of the turbine chamber remote from an axis of the drive shaft to a region of the turbine chamber that is close to the axis of the drive shaft, the cross-connecting channel being configured to allow fluid pressure to rapidly equalize when the pressure medium is removed, wherein the cross-connecting channel is not directly connected to the flowing pressure medium.

2. Medical turbine handpiece according to claim 1, wherein the cross-connecting channel extends through the wall of the turbine chamber into the edge region separated from the turbine chamber.

3. Medical turbine handpiece according to claim 1, wherein the wall of the turbine chamber is formed in multiple parts and the cross-connecting channel is arranged at least in sections in a wall section of a mounting element for the turbine wheel, wherein the mounting element is formed as a spray element for discharging medical fluid.

4. Medical turbine handpiece according to claim 1, wherein the cross-connecting channel has an inlet opening and an outlet opening for the pressure medium.

5. Medical turbine handpiece according to claim 1, comprising a dental turbine handpiece.

6. Medical turbine handpiece according to claim 1, wherein a wall region of the cross-connecting channel is formed in a substantially planar manner with faces that are parallel to each other, wherein several projections or indentations are arranged in the wall region of the cross-connecting channel.

7. Medical turbine handpiece according to claim 6, wherein several projections or indentations are arranged in the wall region of the cross-connecting channel.

8. Medical turbine handpiece according to claim 1, wherein several cross-connecting channels are distributed over a circumference of the turbine chamber.

9. Medical turbine handpiece according to claim 1, wherein the cross-connecting channel is oriented in a radial direction with respect to the axis of the drive shaft.

10. Medical turbine handpiece according to claim 1, wherein an inlet opening of the cross-connecting channel is smaller than a length of the cross-connecting channel.

11. Medical turbine handpiece according to claim 1, wherein the cross-connecting channel is at least partially formed by a thin walled separating web.

12. Medical turbine handpiece according to claim 1, wherein the cross-connecting channel is separated from a return channel for the pressure medium, which supplies pressure medium to the outlet opening.

13. Medical turbine handpiece comprising:
a drive shaft rotatably mounted in a front end region of the handpiece, to which drive shaft a tool can be connected, and
a turbine wheel arranged non-rotatably on the drive shaft and arranged in a turbine chamber formed in the end region, into which turbine chamber a supply line for a flowing pressure medium for driving the turbine wheel opens out at an inlet opening and from which turbine chamber a removal line extends at an outlet opening,
wherein the turbine wheel is sealed to a pressure medium by a sealing face from a region that is axially close with reference to the drive shaft as far as an axially remote edge region, a cross-connecting channel is formed in a wall of the turbine chamber, the cross-connecting channel fluidly connects the axially remote edge region of the turbine chamber to a region of the turbine chamber that is axially close to the drive shaft, the cross-connecting channel being configured to allow fluid pressure to rapidly equalize when the pressure medium is removed, and the cross-connecting channel is not directly connected to the flowing pressure medium.

14. Medical turbine handpiece according to claim 13, wherein a wall region of the cross connecting channel is formed in a substantially planar manner with faces that are parallel to each other, wherein several projections or indentations are arranged in the wall region of the cross-connecting channel.

15. Medical turbine handpiece according to claim 14, wherein several projections or indentations are arranged in the wall region of the cross-connecting channel.

16. Medical turbine handpiece according to claim 13, wherein several cross-connecting channels are distributed over a circumference of the turbine chamber.

17. Medical turbine handpiece according to claim 13, comprising a dental turbine handpiece.

18. Medical turbine handpiece according to claim 13, wherein the cross-connecting channel has an inlet opening that is larger than the outlet opening.

19. Medical turbine handpiece comprising:
a drive shaft rotatably mounted in a front end region of the handpiece, to which drive shaft a tool can be connected, and
a turbine wheel arranged non-rotatably on the drive shaft and arranged in a turbine chamber formed in the end region, into which turbine chamber a supply line for a flowing pressure medium for driving the turbine wheel opens out at an inlet opening and from which turbine chamber a removal line extends at an outlet opening, and
wherein the turbine wheel is sealed to a pressure medium by a sealing face from a region that is axially close with reference to the drive shaft as far as an axially remote edge region, and a cross-connecting channel is formed in a wall of the turbine chamber, and the cross-connecting channel fluidly connects the axially remote edge region of the turbine chamber to a region of the turbine chamber that is axially close to the drive shaft,
wherein the cross-connecting channel has a substantially trapezoidal cross-section.

* * * * *